(12) United States Patent
Alfano et al.

(10) Patent No.: US 7,192,783 B2
(45) Date of Patent: Mar. 20, 2007

(54) STOKES SHIFT EMISSION SPECTROSCOPY FOR DETECTION OF DISEASE AND PHYSIOLOGICAL STATE OF SPECIMEN

(75) Inventors: Robert R. Alfano, Bronx, NY (US); Yuanlong Yang, Elmhurst, NY (US)

(73) Assignee: Research Foundation of the City University of New York, New York, NY (US)

( * ) Notice: Subject to any disclaimer, the term of this patent is extended or adjusted under 35 U.S.C. 154(b) by 716 days.

(21) Appl. No.: 10/684,896

(22) Filed: Oct. 14, 2003

(65) Prior Publication Data

US 2004/0152203 A1  Aug. 5, 2004

Related U.S. Application Data

(60) Provisional application No. 60/444,869, filed on Feb. 5, 2003.

(51) Int. Cl.
*G01N 21/62* (2006.01)
*G01N 21/63* (2006.01)
*G01N 21/64* (2006.01)
*G01N 21/31* (2006.01)
*A61B 5/00* (2006.01)

(52) U.S. Cl. ............ 436/171; 436/63; 436/64; 436/164; 422/82.05; 356/317; 356/318; 250/459.1; 435/29

(58) Field of Classification Search .......... 436/63, 436/64, 164, 171, 172; 422/82.05, 82.08, 422/82.09; 356/300, 317, 318; 250/458.1, 250/459.1; 435/4, 5, 29
See application file for complete search history.

(56) References Cited

U.S. PATENT DOCUMENTS

| 5,131,398 | A  | * | 7/1992  | Alfano et al. | 600/476 |
| 5,769,081 | A  | * | 6/1998  | Alfano et al. | 600/476 |
| 6,080,584 | A  | * | 6/2000  | Alfano et al. | 436/63  |
| 6,091,985 | A  | * | 7/2000  | Alfano et al. | 600/476 |
| 6,151,522 | A  | * | 11/2000 | Alfano et al. | 600/473 |
| 6,580,941 | B2 | * | 6/2003  | Webb          | 600/478 |

FOREIGN PATENT DOCUMENTS

JP  4-339240  * 11/1992

OTHER PUBLICATIONS

Alfano et al. Stokes Shift Emission Spectroscopy of Human Tissue and Key Biomolecules. IEEE Journal of Selected Topics in Quantum Electronics, vol. 9, No. 2, Mar./Apr. 2003, pp. 148-153.*

Alfano et al. Stokes Shift Emission Spectroscopy of Key Biomolecules in Human Tissues. Proceedings of SPIE, vo. 5326, 2004, pp. 1-7.*

* cited by examiner

*Primary Examiner*—Maureen M. Wallenhorst
(74) *Attorney, Agent, or Firm*—Cohen Pontani Lieberman & Pavane LLP

(57) ABSTRACT

The Stokes shift emission spectra were measured for various samples, including tissues containing photoactive bio-molecules such as tryptophan, elastin, collagen, NADH and flavin. This new approach allows for the extraction of new information not easily obtained from the excitation and or fluorescence spectra of the same samples. For example, Stokes shift spectroscopy of tissue samples can detect disease states in humans and animals.

48 Claims, 13 Drawing Sheets

STOKES SHIFT EMISSION SPECTROSCOPY FOR DETECTION OF DISEASE AND PHYSIOLOGICAL STATE OF SPECIMEN

RELATED APPLICATIONS

This application claims priority from U.S. Provisional Patent Application Ser. No. 60/444,869, which was filed on Feb. 5, 2003.

BACKGROUND OF THE INVENTION

1. Field of the Invention

The present invention relates generally to the fields of chemical analysis and biomedical diagnostics, and more particularly, to the use of fluorescence and absorption associated with the Stokes shift to determine the molecular components.

2. Description of the Related Art

The emission and absorption of organic molecules in different hosts has been studied since Newton's work on color and dispersion. Information on the state of matter has been obtained by measuring the emission and absorption spectra. For over four decades, spectroscopy has played an important role in understanding the fundamental processes that occur in biology, chemistry, and solid-state physics. In the context of biology, the presence of intrinsic fluorophores such as tryptophan, collagen, elastin, NADH, and flavins in animal and human tissues offer potential opportunities to probe the morphological changes occurring in diseased tissues using cw and time-resolved fluorescence spectroscopy [1].

Since 1984, fluorescence spectroscopy has been used as diagnostic tool to separate cancer, benign and surrounding tissue regions [2-5]. Typically, a tissue is excited at a given wavelength to emit radiation at different wavelengths, which characterize the tissue. The wavelengths from UV to blue range (280–520 nm) excite proteins in the tissue associated with changes in structure and molecular content, which gives their spectral fingerprints. The particles in the tissue include tryptophan, collagen, elastin, and NADH.

The underlying dynamics of organic biomolecules occur on the energy configuration coordinate (E-Q) diagram [6-8], where E≡energy and Q≡normalized dimensionless lattice displacement coordinate. The electronic, vibration and rotational states associated with ground and excited states of a biomolecule are denoted on the E-Q diagram. The absorption and emission transition occurs as vertical transition between the states on the E-Q diagram (see FIG. 1). The time evolution of the process can be followed on E-Q diagram during nonradiative lattice relaxation and excitation [1]. The ground and excited states are located at different equilibrium Q coordinate positions due to difference in electronic-lattice coupling. The difference in electronic-lattice coupling is denoted by the Huang-Rhys parameters, S.

Typically, the peaks of the absorption and the emission occur at different wavelengths. The emission band occurs at lower energy than the excitation band. The shift of the emission and absorption peaks is known as the Stokes shift given by $2S\hbar\omega$. The Stokes shift depends on the polarization of the host environment surrounding the emitting organic molecule. Large shifts are observed for a polar surrounding, such as water. There is dynamic change in the location of energy states associated with this interaction between dipole moment of transition and the surrounding host molecules during excitation and emission [8].

SUMMARY OF THE INVENTION

Therefore, one object of the present invention is to develop a new spectroscopic method combining fluorescence and absorption, which is associated with the Stokes shift. This method is called STOKES SHIFT SPECTROSCOPY (SSS).

Another object of the present invention is to develop a new spectroscopic method which has the potential of being much more sensitive for detecting changes associated with native biomarkers in biological tissue and cells that characterize a disease state such as a cancer, precancer, normal or atherosclerosis.

In accordance with one embodiment of the present invention, a method of testing a sample comprises:
  a. exciting the sample with excitation radiation and thereby generating emission radiation;
  b. varying the excitation radiation by regulating a parameter selected from the group consisting of wavelength and frequency of the excitation radiation; and
  c. synchronously scanning the excitation radiation and the emission radiation to produce a spectrum;
  where a constant interval between the regulated parameter of the excitation radiation and that of the emission radiation is maintained during the synchronous scanning; and
  the constant interval is maintained to be substantially the Stokes shift of at least one component of the sample.

In accordance with another embodiment of the present invention, a method of testing a sample comprises:
  a. exciting the sample with excitation radiation and thereby generating emission radiation;
  b. varying the excitation radiation by regulating a parameter selected from the group consisting of wavelength and frequency;
  c. synchronously scanning the excitation radiation and the emission radiation to produce a first spectrum, wherein a constant interval between the regulated parameter of the excitation radiation and that of the emission radiation is maintained during the synchronous scanning;
  d. adjusting the constant interval and repeating the steps of a)–c) at least one time to produce at least a second spectrum; and
  where the constant interval is maintained or adjusted to substantially be the Stokes shift of at least one component of the sample.

The Stokes shift emission is measured at a fixed wavelength shift between the absorption and emission wavelengths, $\Delta\lambda=\lambda_E-\lambda_A$ giving the convolution of absorption and emission spectral profiles. The intensity emission is measured and scanned at emission wavelength fixed $\Delta\lambda=\lambda_E-\lambda_A$. The Stokes shift $\Delta\lambda=\lambda_E-\lambda_A$ can be written in frequency domain $\Delta\nu=\nu_A-\nu_E$, and expressed in units of Hz, THz or $cm^{-1}$. In this manner, the key molecules involved in the material such as tissue will be highlighted.

In Stokes shift emission spectrum, the excitation and emission wavelength is scanned synchronously with a fixed value of $\Delta\lambda$ between excitation and emission wavelength. The intensity of emission is measured at $\lambda_E$. The different molecules in the sample can be excited and revealed, which is much different than fluorescence spectrum excited at a fixed wavelength. The intensity of Stokes shift emission depends on the value of $\Delta\lambda$ for each molecular component present in the sample. The maximum intensity occurs when $\Delta\lambda$ is near equal to Stokes Shift of particular molecule type excited. The fluorescence peaks of key molecules in tissue can be obtained in one scan by using Stokes shift emission spectrum. The position of peak can be determined by using multiple peaks fit to the SS spectrum. SS spectrum will play an important role in the disease detection, such as cancer and atherosclerosis detection.

In one preferred embodiment, at least one optical fiber is used to propagate the excitation radiation to the sample, or to propagate the emission radiation from the sample to a video system for scanning, or both. The optical fiber may be used as one component of an endoscopic system.

The various features of novelty, which characterize the invention, are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

BRIEF DESCRIPTION OF THE DRAWINGS

In the drawings:

FIG. 10(*b*) is a SS spectrum for normal and cancer tissue in frequency domain (v).

DETAILED DESCRIPTION OF THE PRESENTLY PREFERRED EMBODIMENTS

In accordance with the present invention, the tissue to be tested may be breast, urinary, colon, stomach, brain, prostate, or GYN tissue. The tissue or cell may be in a state selected from the group consisting of normal, cancer, pre-cancer, and atherosclerosis. The wavelength of the excitation may be varied in the range of 200 to 800 nm.

For testing biological molecules of tryptophan, NADH, and flavin, samples of these molecules were obtained from Sigma Company. The tissues were supplied from National Disease Research Interchange (NDRI) under IRB. It was fresh and neither chemically treated nor frozen prior to spectroscopic A mixture solution containing tryptophan, NADH and flavin was made for the test measurements. The concentration of each component in this composite solution was adjusted to make the fluorescence intensity of each component similar. The Stokes Shift emission spectrum was performed using an automated dual lamp-based spectrophotometer (Mediciscience Technology Corp. CD scanner) by selecting synchronizes scan mode. The wavelength interval between excited and emission monochromators were adjusted to $\Delta\lambda=\lambda$hd $E-\lambda_A$=10, 20, 30, ... 200 nm or in frequency $\Delta v=v_A-v_E$. The value should be calculated according to corresponding $\Delta\lambda$ value or $\Delta v$ value.

The relationship between wavelength shift $\Delta\lambda$(nm), frequency shift $\Delta v$(THz) and frequency shift $\Delta v$(cm$^{-1}$) are shown in the Table 1: (1THz)=33.3564 cm$^{-1}$

TABLE 1

| $\Delta\lambda$ (nm) | $\lambda_1$ (nm) | $\lambda_2$ (nm) | $\Delta v = (C * \Delta\lambda)/(\lambda_1 * \lambda_2)$ (THz) | $\Delta v$ (cm$^{-1}$) |
|---|---|---|---|---|
| 10 | 200 | 210 | 71.4 × 10$^{12}$ = 71.4 | 2381.65 |
|  | 300 | 310 | 32.3 × 10$^{12}$ = 32.3 | 1077.41 |
|  | 400 | 410 | 18.3 × 10$^{12}$ = 18.3 | 610.42 |
|  | 500 | 510 | 11.8 × 10$^{12}$ = 11.8 | 393.61 |
|  | 600 | 610 | 8.2 × 10$^{12}$ = 8.2 | 273.52 |
| 40 | 200 | 240 | 250 × 10$^{12}$ = 250 | 8339.10 |
|  | 300 | 340 | 117.6 × 10$^{12}$ = 117.6 | 3922.72 |
|  | 400 | 440 | 68.2 × 10$^{12}$ = 68.2 | 2274.91 |
|  | 500 | 540 | 44.4 × 10$^{12}$ = 44.4 | 1481.02 |
|  | 600 | 640 | 31.3 × 10$^{12}$ = 31.3 | 1044.06 |
| 50 | 200 | 250 | 300 × 10$^{12}$ = 300 | 10006.92 |
|  | 300 | 350 | 142.9 × 10$^{12}$ = 142.9 | 4766.63 |
|  | 400 | 450 | 83.3 × 10$^{12}$ = 83.3 | 2778.59 |
|  | 500 | 550 | 54.5 × 10$^{12}$ = 54.5 | 1817.92 |
|  | 600 | 650 | 38.5 × 10$^{12}$ = 38.5 | 1284.22 |
| 100 | 200 | 300 | 500 × 10$^{12}$ = 500 | 16678.20 |
|  | 300 | 400 | 250 × 10$^{12}$ = 250 | 8339.10 |
|  | 400 | 500 | 150 × 10$^{12}$ = 150 | 5003.46 |
|  | 500 | 600 | 100 × 10$^{12}$ = 100 | 3335.64 |
| 150 | 200 | 350 | 642.9 × 10$^{12}$ = 642.9 | 21444.83 |
|  | 300 | 450 | 333.3 × 10$^{12}$ = 333.3 | 11117.69 |
|  | 400 | 550 | 204.5 × 10$^{12}$ = 204.5 | 6821.38 |
|  | 500 | 650 | 138.5 × 10$^{12}$ = 138.5 | 4619.86 |

Figure 1:
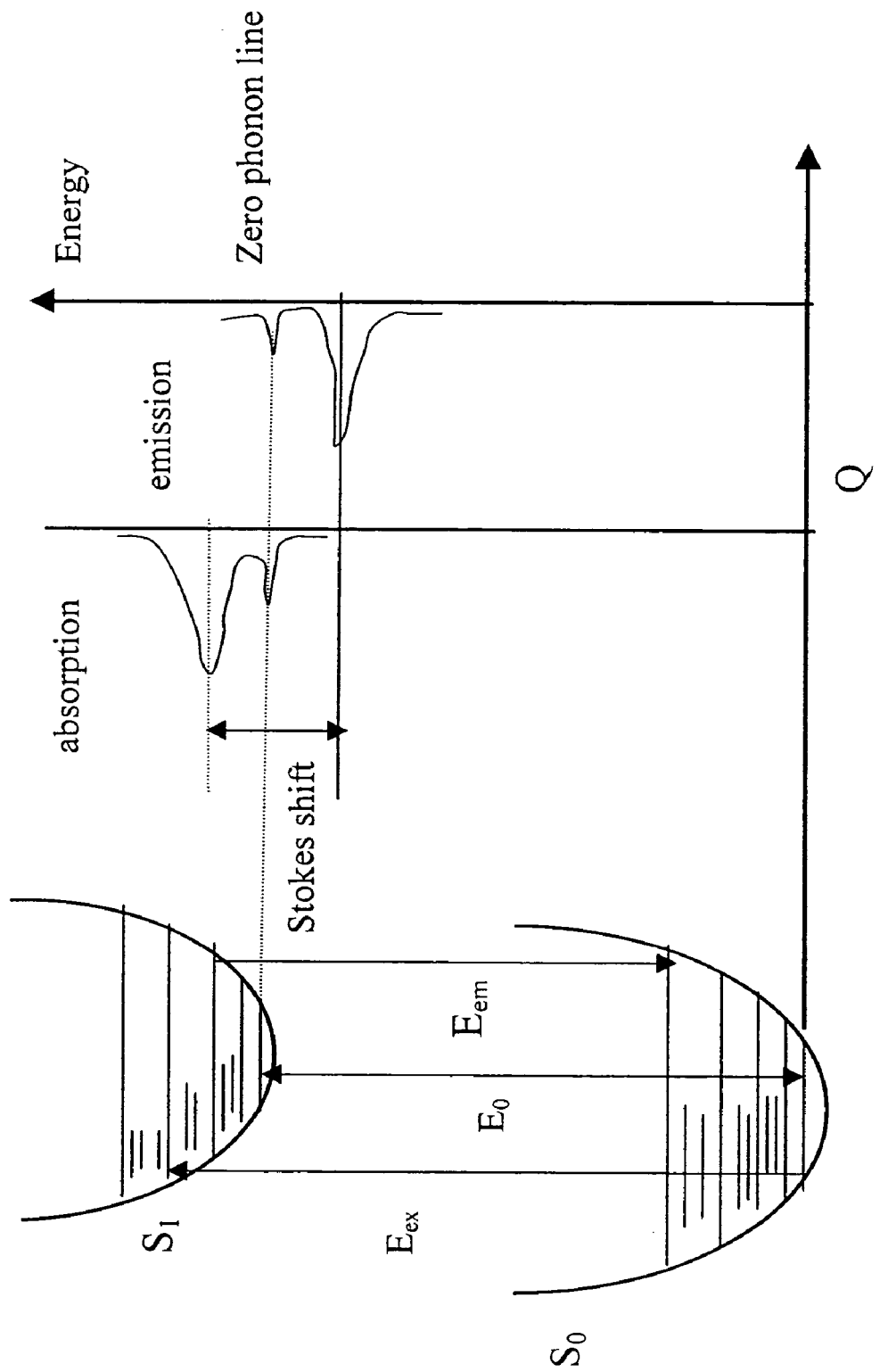
FIG. 1 is an energy configuration coordinate diagram for organic molecules showing absorption and emission transitions and the relaxation process.
Figure 2:
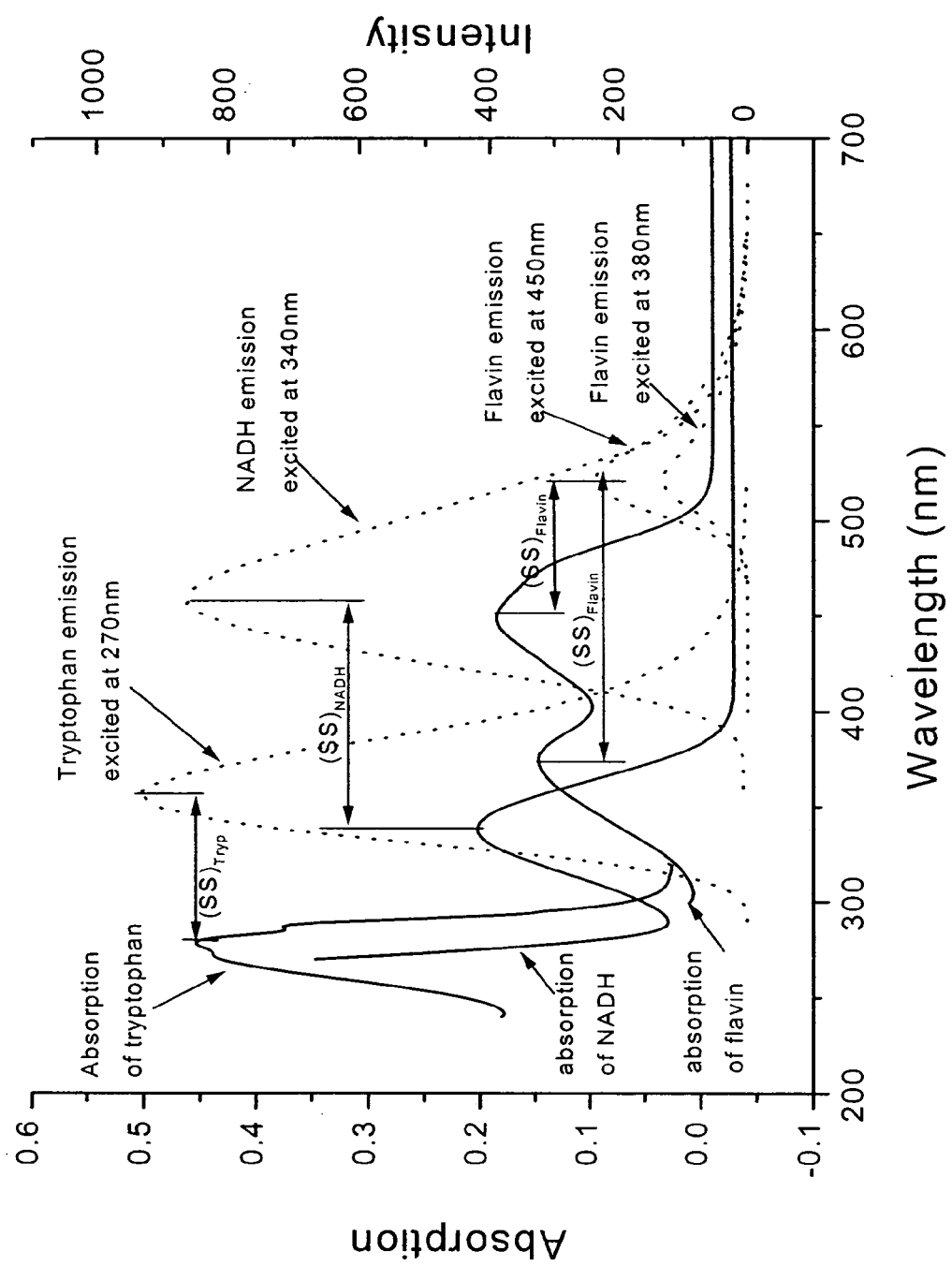
FIG. 2 shows absorption and emission spectra and STOKES SHIFTS (SS) of tryptophan, NADH and flavins.

The combined emission and absorption spectrum of biomolecules solution of tryptophan, NADH and flavin was measured and displayed in FIG. 2. The curves show the absorption and emission peaks associated with each molecule are different. This difference is called Stokes shift (SS). The SS spectroscopy (see FIG. 10) in frequency domain is a measure of overlap region of absorption $A(v)$ and emission $I_E(v)$ spectra (see FIG. 10)

$$I_E(v')=\int \sigma A(v)E(v-v')dv$$

$$v=v'+\Delta v$$

The range of $\Delta\lambda$ gives a measure of the overlap resolution and correlation of two spectra. The measured Stokes Shift values $\Delta\lambda=\lambda_E-\lambda_A$ for different molecules are listed in Table 2 as follows.

TABLE 2

Absorption and emission peaks and Stokes shift of key bio-molecules from fluorescence and absorption spectrum

| Molecular | Absorption peak (nm) | Emission peak (nm) | Stokes shift (nm) |
|---|---|---|---|
| Tryptophan (T) | 280 | 356 | 76 |
| Collagen (C) | 340 | 380 | 40 |
| NADH (N) | 340 | 460 | 120 |
| Flavin (F) | 375 | 520 | 145 |
|  | 450 | 520 | 70 |

Note:
It is a common practice to measure Stokes Shift in $\Delta\lambda$ space for convenience; however, frequency shift gives correct SS spectrum.

If the regulated parameter in accordance with the present invention is wavelength, the constant interval maintained or adjusted may be within the range of about 40 to 145 nm, preferably about 40 to 120 nm. When the regulated parameter is frequency, the constant interval may be within the range of about 5 to 500 THz or 150 to 15,000 cm$^{-1}$, preferably 10 to 500 THz or 300 cm$^{-1}$ to 15,000 cm$^{-1}$.

Figure 3:
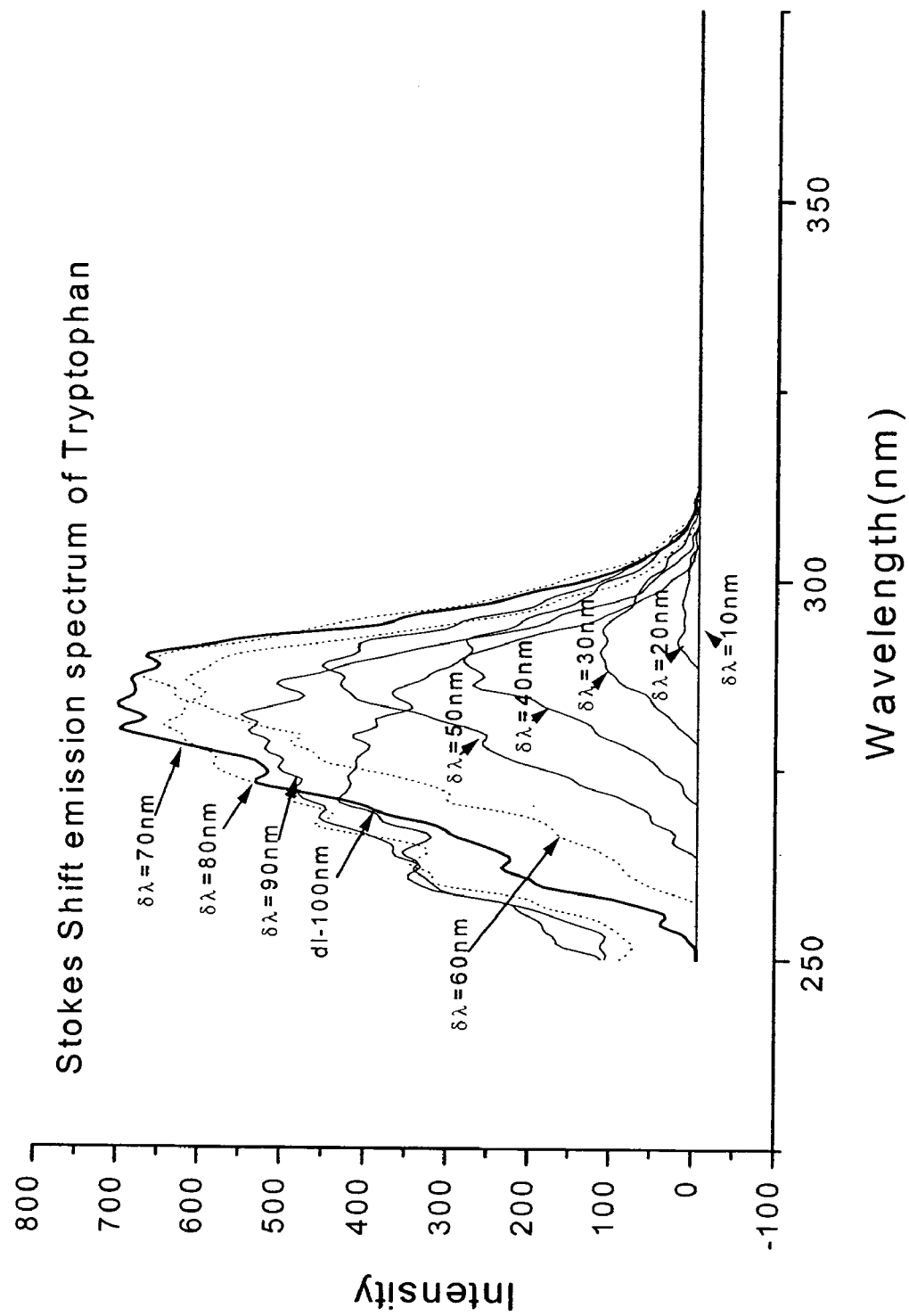
FIG. 3 shows Stokes shift emission spectrum of tryptophan for different $\Delta\lambda$ values.

The Stokes shift emission spectrum of a tryptophan solution with different $\Delta\lambda$ value from 10 nm to 100 nm is shown in FIG. 3. The emission intensity is varied with $\Delta\lambda$. When $\Delta\lambda$ equals to the Stokes shift, the emission intensity is at a maximum. In FIG. 3, the maximum of the emission intensity is at (SS) $\Delta\lambda$=70 nm, which is consistent with the result displayed in Table 2 as measured in wavelength space. These values will change in frequency space. In accordance with the present invention, $\Delta\lambda$ value may be adjusted in an increment within the range of 5–50 nm, 5–100 THz, or 50 to 3000 cm$^{-1}$.

Figure 4:
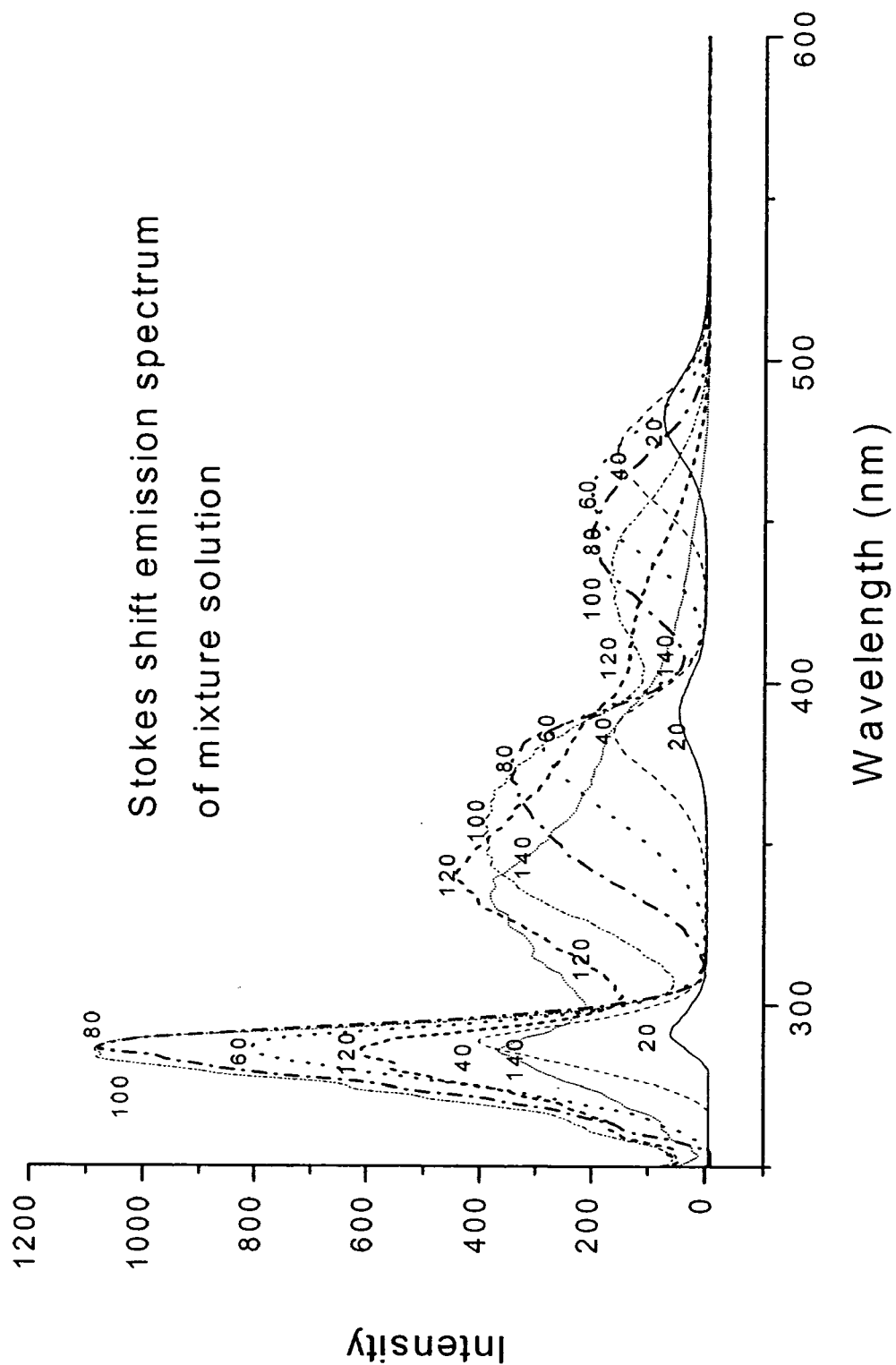
FIG. 4 shows Stokes shift emission spectrum of a mixture solution containing tryptophan NADH and flavin with different $\Delta\lambda$ values.

FIG. 4 shows the Stokes shift emission spectrum of a mixture solution composed of tryptophan, NADH and flavin in water with different $\Delta\lambda$. The emission peak for each molecular component was found in the Stokes shift emission spectrum. The peak amplitude for various molecules with $\Delta\lambda$ value is associated with each molecular component. The maximum intensity occurs when (SS) $\Delta\lambda$ nearly equal to Stokes Shift of the particular molecule excited. For this mixed solution the Stokes shift is near 80 nm, and 120 nm for tryptophan, and NADH, and 140, 80 nm for flavin, respectively. These results from mixture solution are a little larger than the results from solutions containing each of the molecular components alone, which are listed in Table 2.

Figure 5:
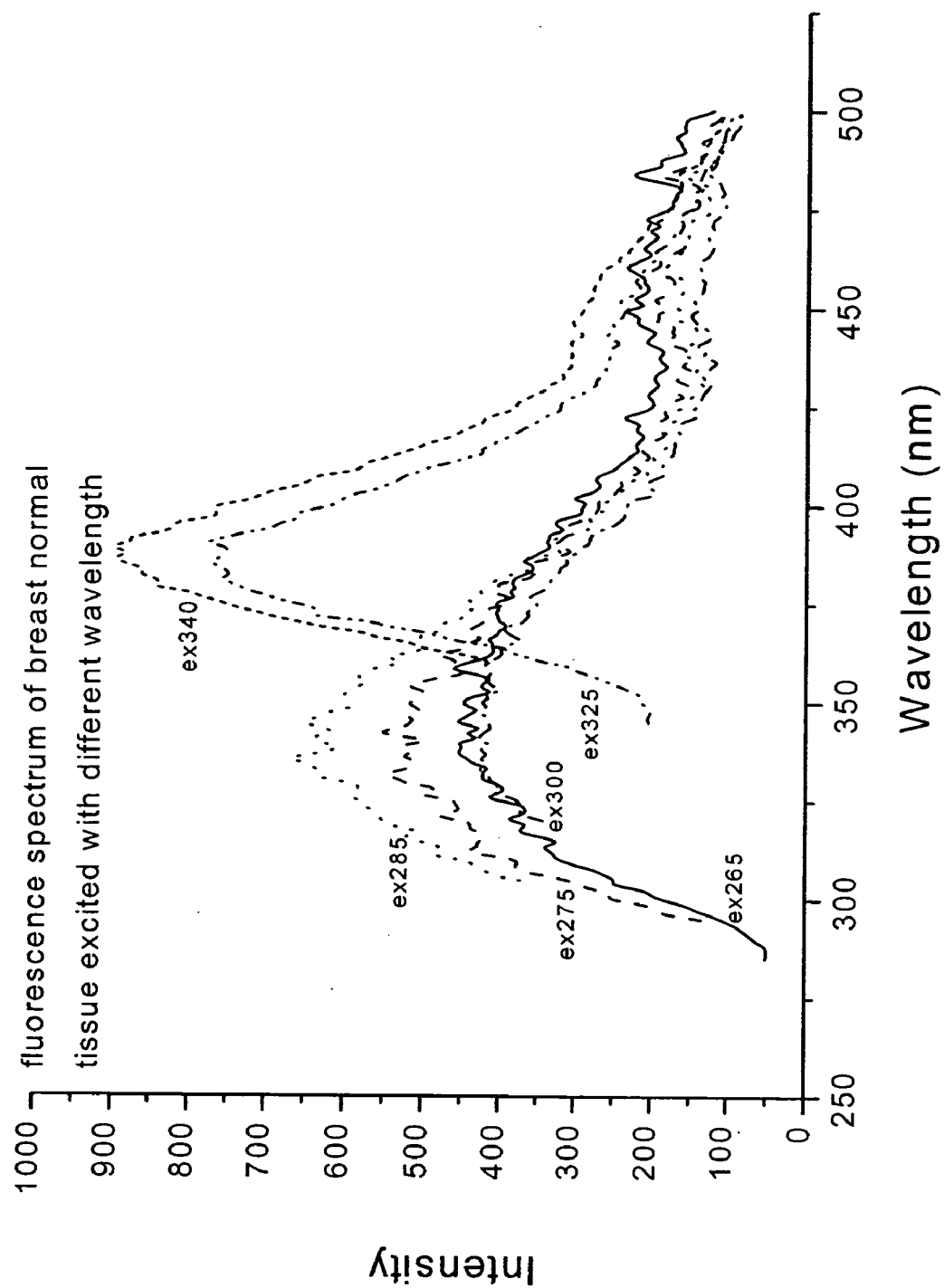
FIG. 5 shows fluorescence spectrum of normal breast tissue excited with different excitation wavelengths.

FIG. 5 shows the test fluorescence spectrum of normal breast tissue excited at different wavelengths. From the fluorescence peak position, one can recognize tryptophan, collagen, and NADH associated with the different excitation wavelengths.

Figure 6:
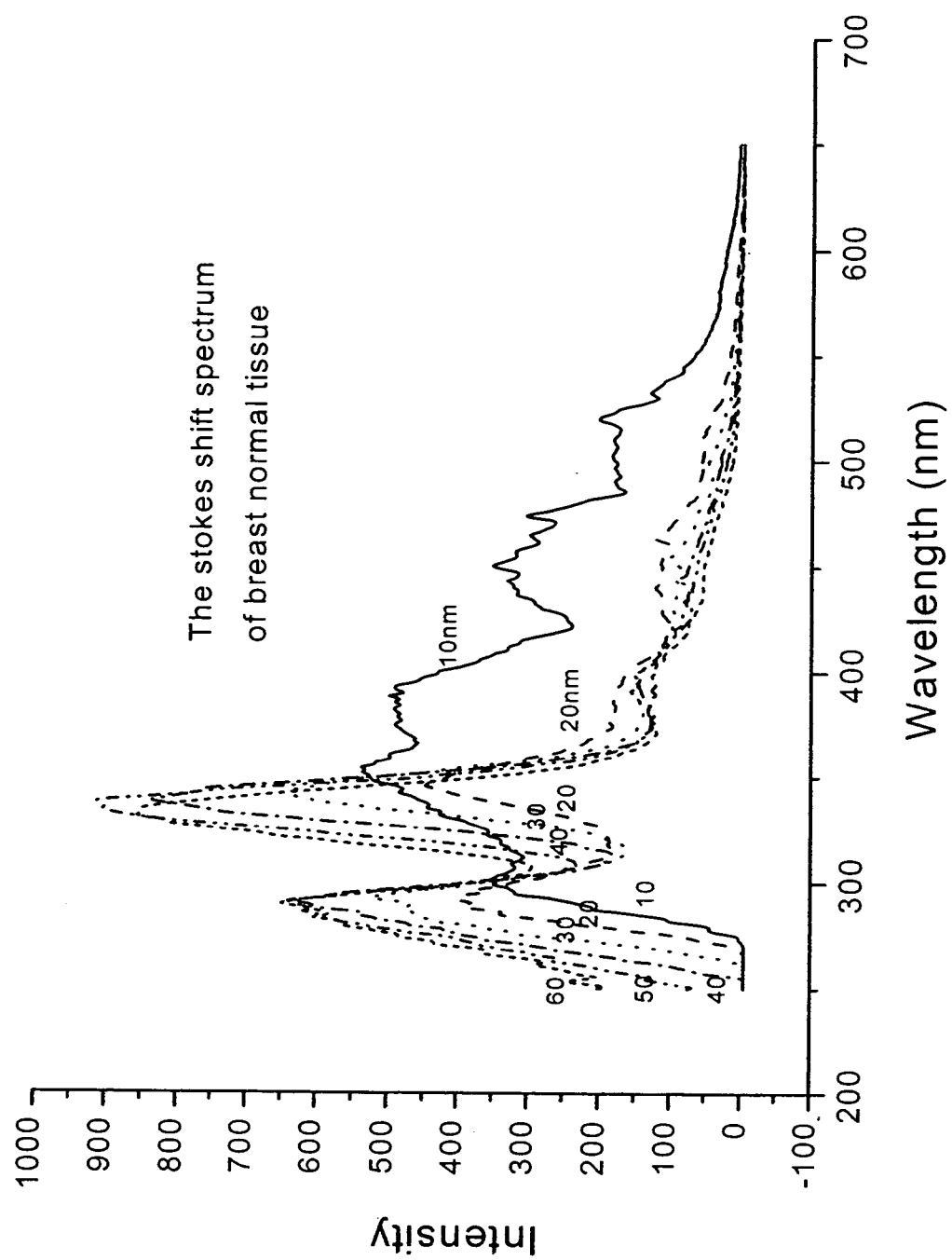
FIG. 6 shows Stokes shift emission spectrum of normal breast tissue with different $\Delta\lambda$ values as marked on each of the profiles.

The Stokes shift emission spectrum of normal breast tissue with different $\Delta\lambda$ value is displayed in FIG. 6. The intensity of emission peak changes with $\Delta\lambda$ value and the $\Delta\lambda$ value of maximum intensity is different because of the presence of different molecular components. The spectral curves in FIG. 6 are more sensitive to the molecules in tissue than those conventional fluorescence curves displayed on FIG. 5.

Figure 7:
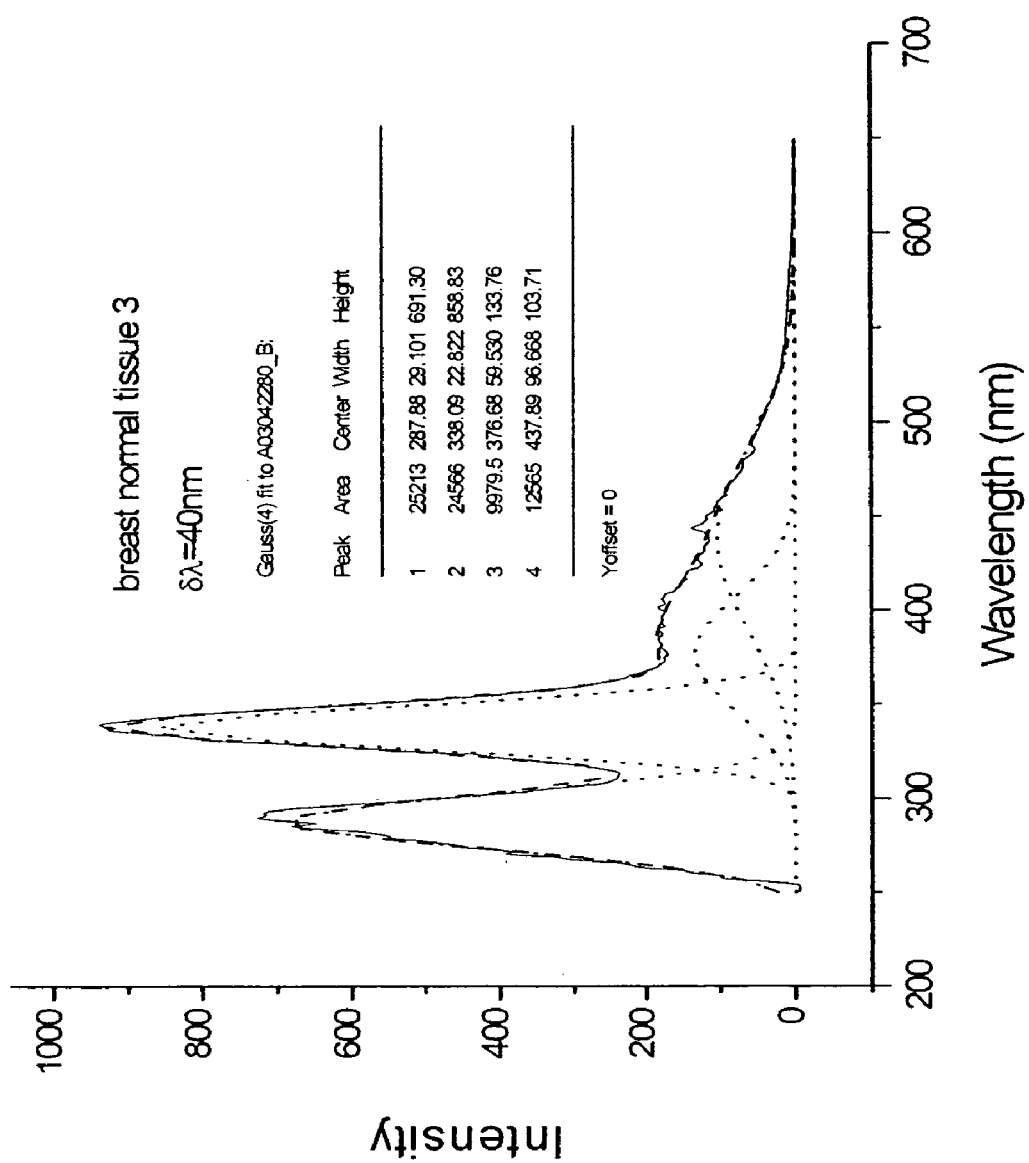
FIG. 7 shows a fit to Stokes shift emission for normal breast tissue curve using software from Microsoft Office "Origin".

FIG. 7 displays a calculated multiple-curve fit of Stokes shift spectrum with $\Delta\lambda$~50 nm for breast tissue. Fitted peak positions are given in Table 3 as follows:

TABLE 3

Parameters used for multiple curve fit of Stokes shift spectrum of breast from S.S. ($\Delta\lambda$ = 50 nm)

| | Peaks | | | | |
|---|---|---|---|---|---|
| | 1 | 2 | 3 | 4 | 5 |
| Excited wavelength (nm) | 280.28 | 332.23 | 395.58 | 459.04 | 528.52 |
| Emission wavelength (nm) | 330.38 | 382.23 | 445.58 | 509.04 | 578.28 |
| Suggested molecule | Tryptophan | Collagen | NADH | Flavin | Porphyrin |

Emission wavelength = excited wavelength + 50 nm

For spectrum with a different $\Delta\lambda$ value, the fit to the curve peaks is nearly the same since the Stokes shift is dependent on the molecular components present (tryptophan, NADH, collagen, flavin and porphyrin).

Figure 8:
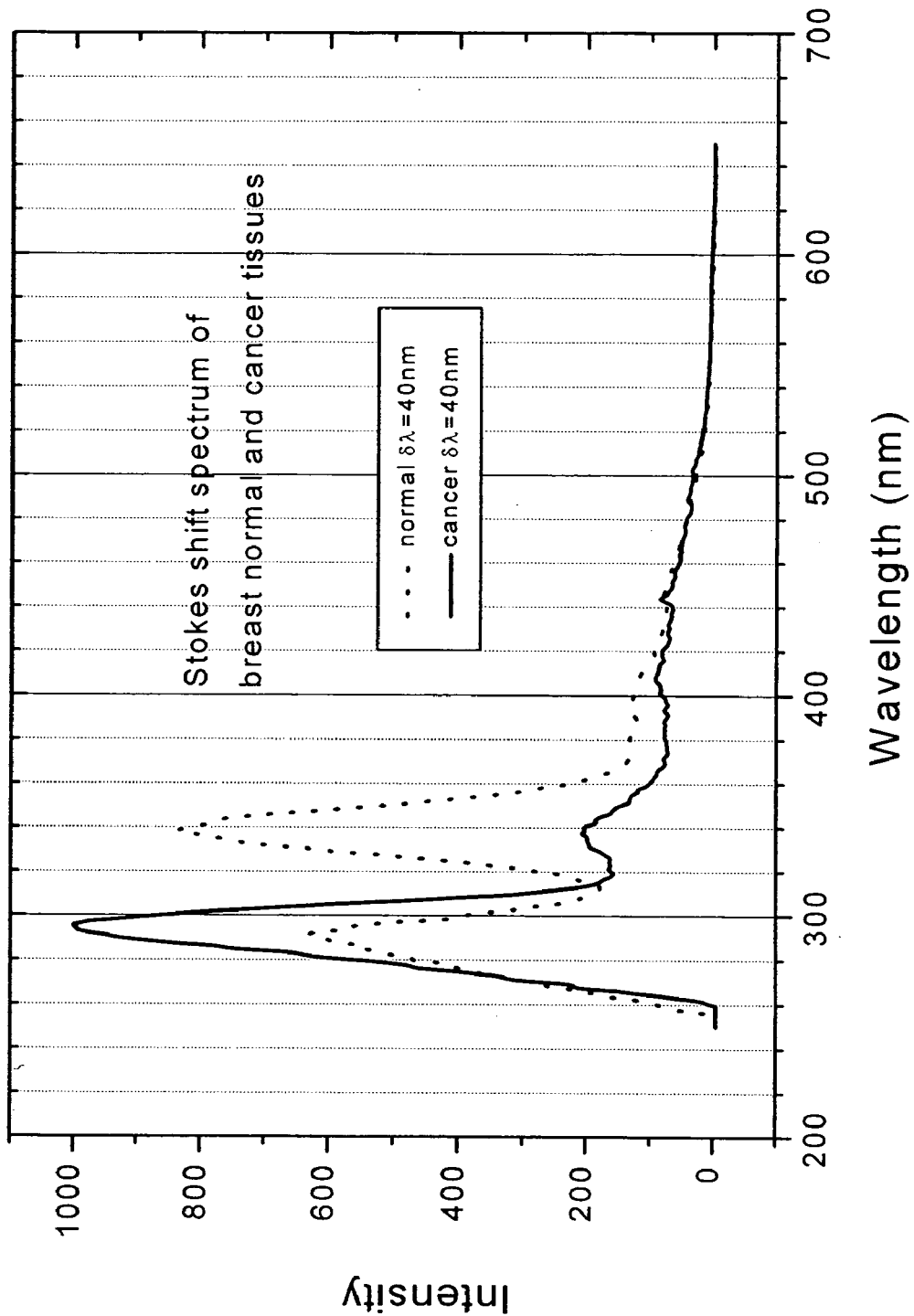
FIG. 8 shows Stokes Shift ("SS") spectra for cancer and normal tissue.

FIG. 8 shows SS curves for normal and cancer tissues. As shown in FIG. 8, to determine whether the tissue sample is cancerous, precancerous, or normal, one can compare the ratio between the intensities at at least two wavelengths or frequencies of the spectrum of the tissue sample to that of another tissue whose condition is known. In addition, one can compare the peak position at at least one wavelength or frequency of the spectrum of the tissue sample to that of another tissue whose condition is known. For example, the difference either on the ratio of peak amplitude of $I_{290}/I_{340}$ or on the peak position of the first peak of these two curves give the diagnostic means of distinguishing cancerous from normal regions of a tissue in vivo. Usually the cancer has higher ratio value of $I_{290}/I_{340}$, while the normal tissue has lower ratio value of $I_{290}/I_{340}$. Additionally, the first peak position of normal tissue of SS spectrum is 288.08±0.80 and for cancer, it is shifted to 291.49±1.60. The wavelength difference of the first peak position of normal tissue and abnormal tissue (such as cancerous tissue) ($\Delta\lambda$) is typically greater than 1 nm. This difference reflects a change in the protein. The SS spectrum (FIG. 8) highlights the component more than conventional fluorescence spectrum (see FIG. 12).

Figure 9:
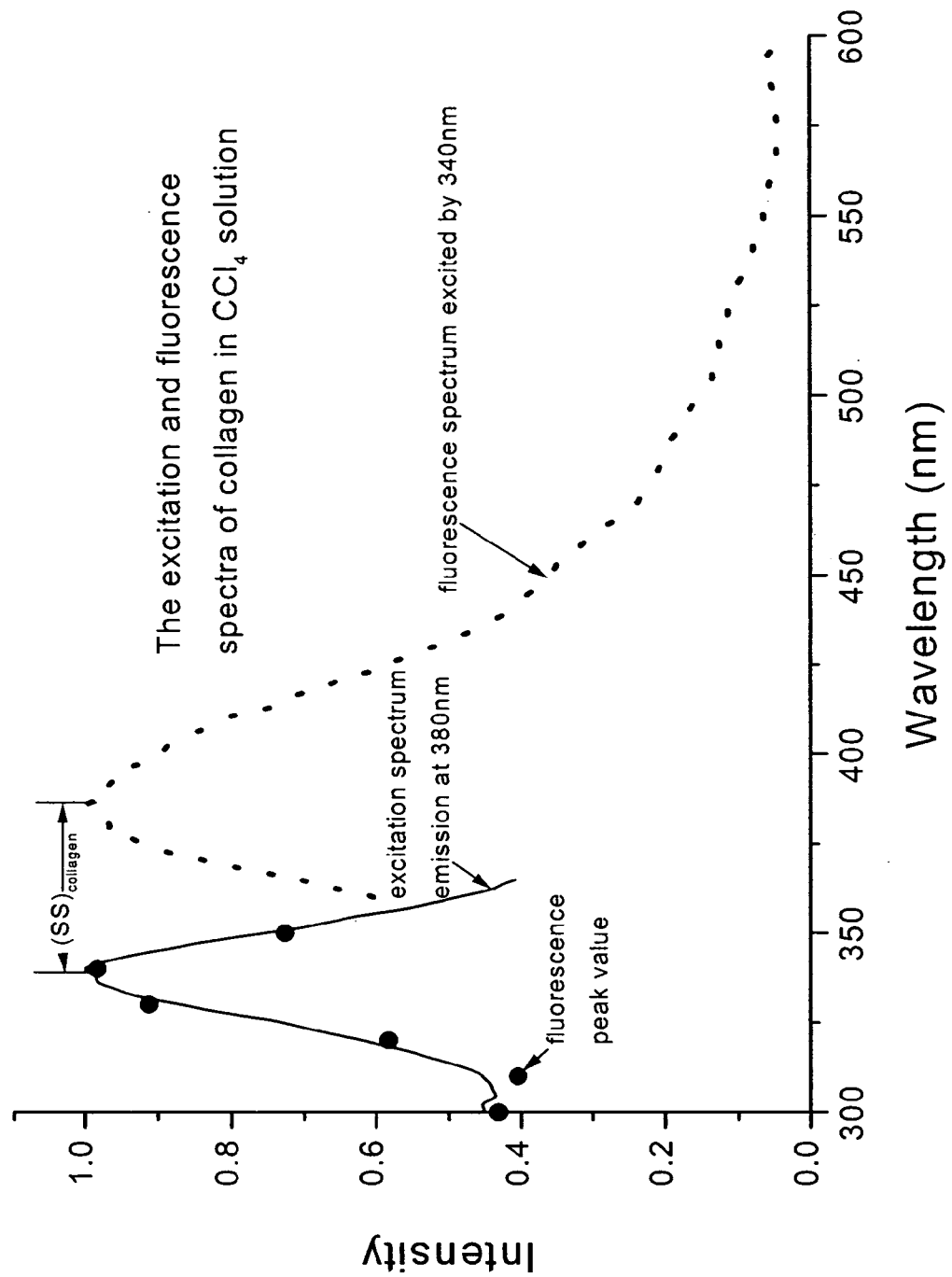
FIG. 9 shows the SS spectrum of collagen.

FIG. 9 shows the SS spectrum of collagen.

Figure 10A:
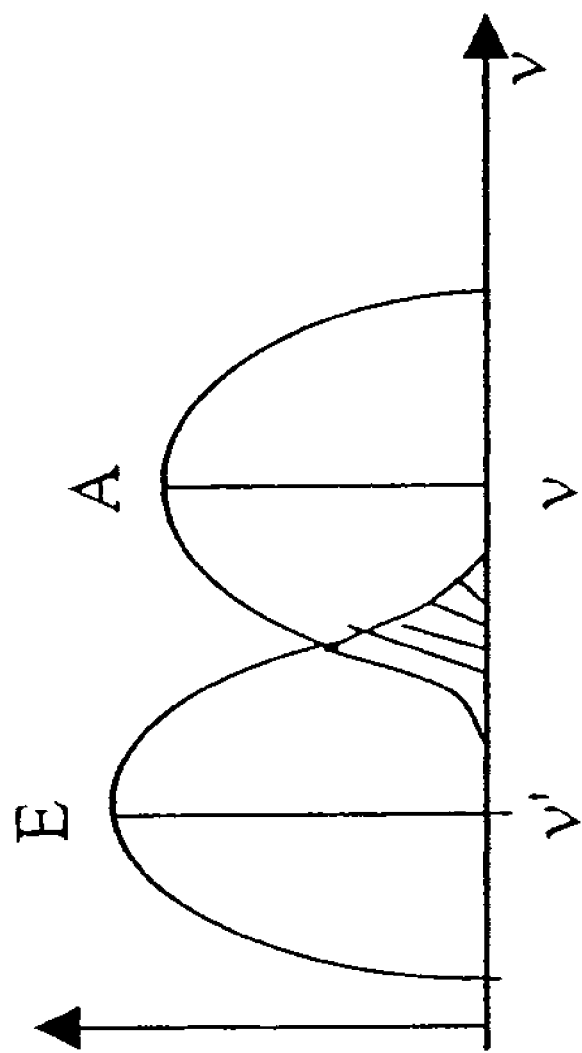
FIG. 10(*a*) is a SS spectrum illustrating overlap of absorption $A(v)$ and emission $I_E(v)$ spectra in frequency domain for normal and cancer tissue in Thz where $(\Delta v)_{average}$=74 THz.
Figure 10B:
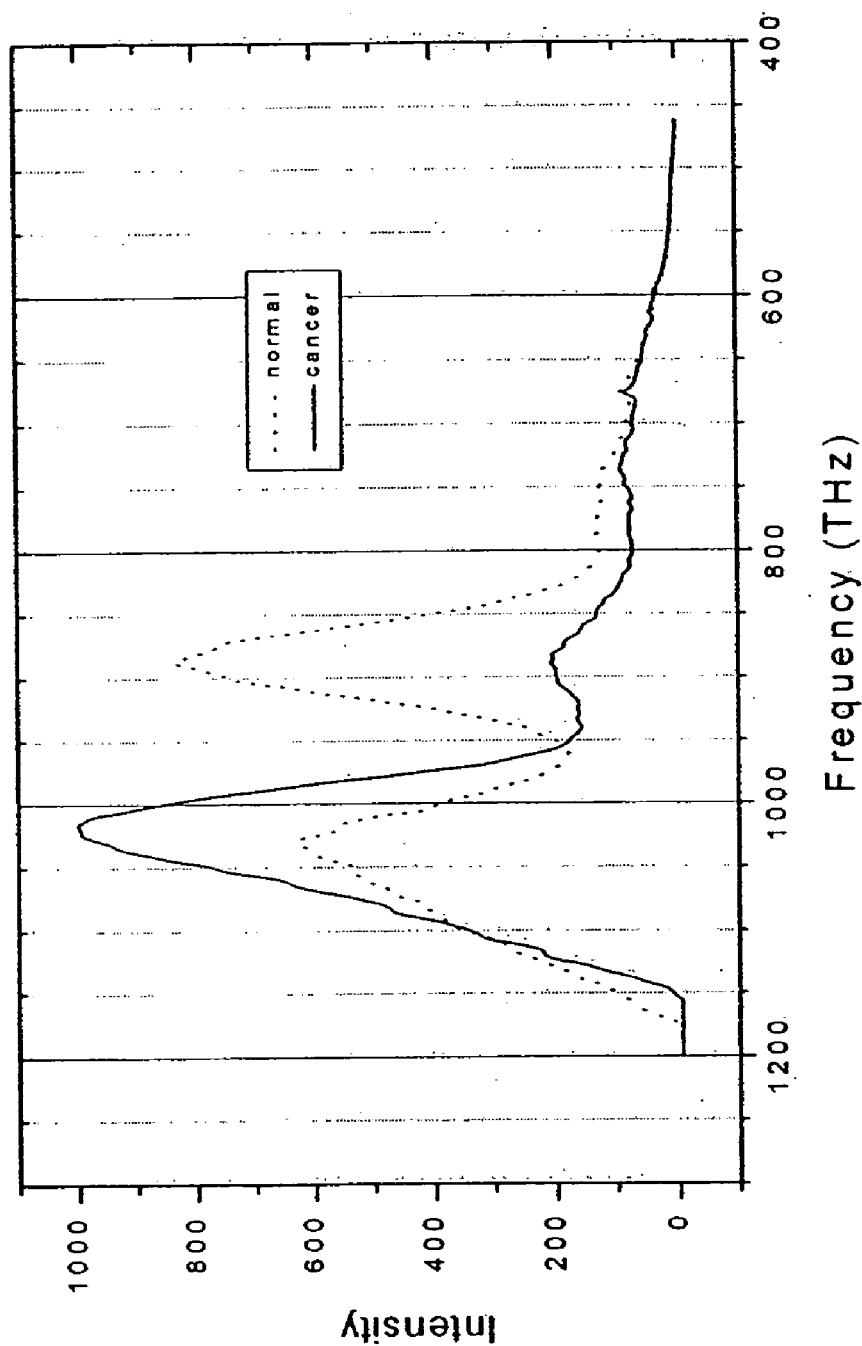

FIG. 10 shows SS in THz for $(\Delta v)_{average}$=74 THz

Figure 11:
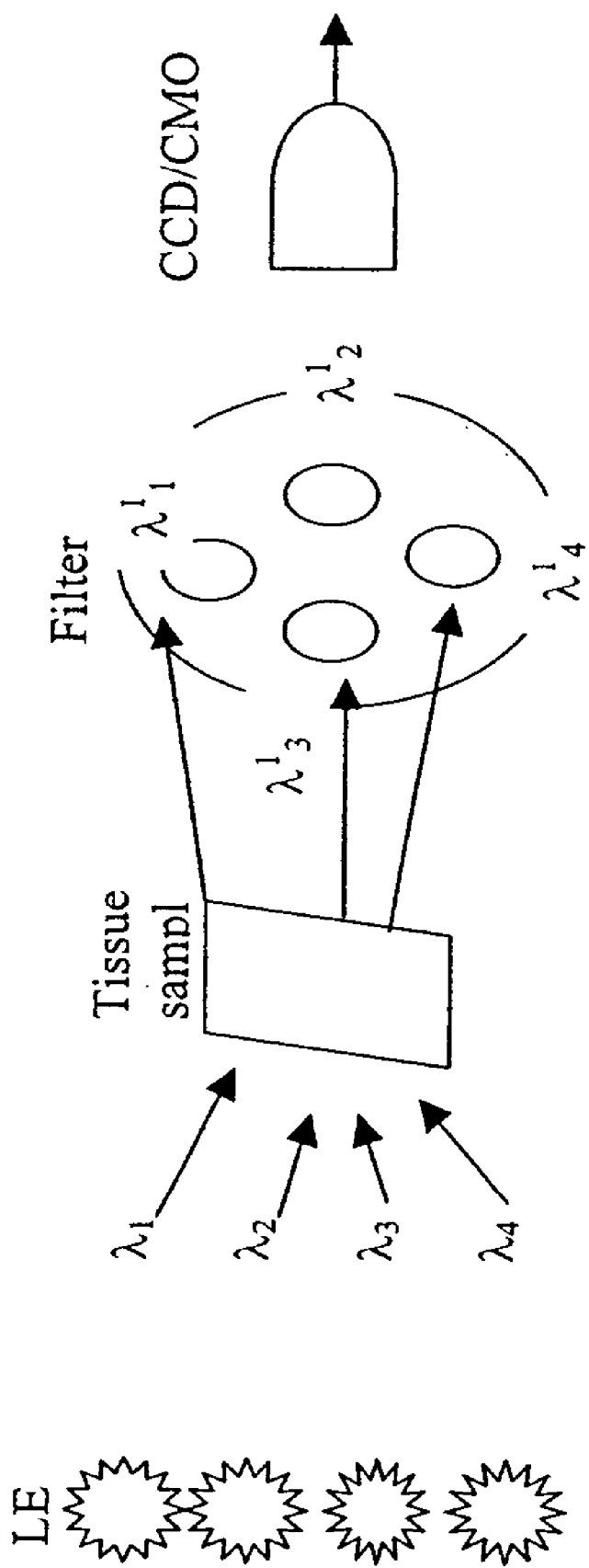
FIG. 11 shows using pairs of LED ($\lambda_i$ and photo-detector) to excite tissue and filter to detect emission at ($\lambda_j'$) arranged at fixed $\Delta\lambda=\lambda_i-\lambda_j'$ where I=1, 2, ... n.

FIG. 11 shows a plurality of LEDs used to excite the sample at different excitation wavelengths and detecting by means of a video system such as CCD or CMOS the emission at different wavelengths with a constant interval between the wavelengths of the excitation radiation and the emission radiation. A plurality of spectral pass band filters is used to filter the excitation radiation in the synchronous scanning step. The video system to record the excitation radiation and the emission radiation in the synchronous scanning may be CCD, CMOS, PMT, photodetector and avalanche diode, where PMT is a preferable one. CCD or CMOS video system is used to record the excitation radiation and the emission radiation in the synchronous scanning step.

Figure 12:
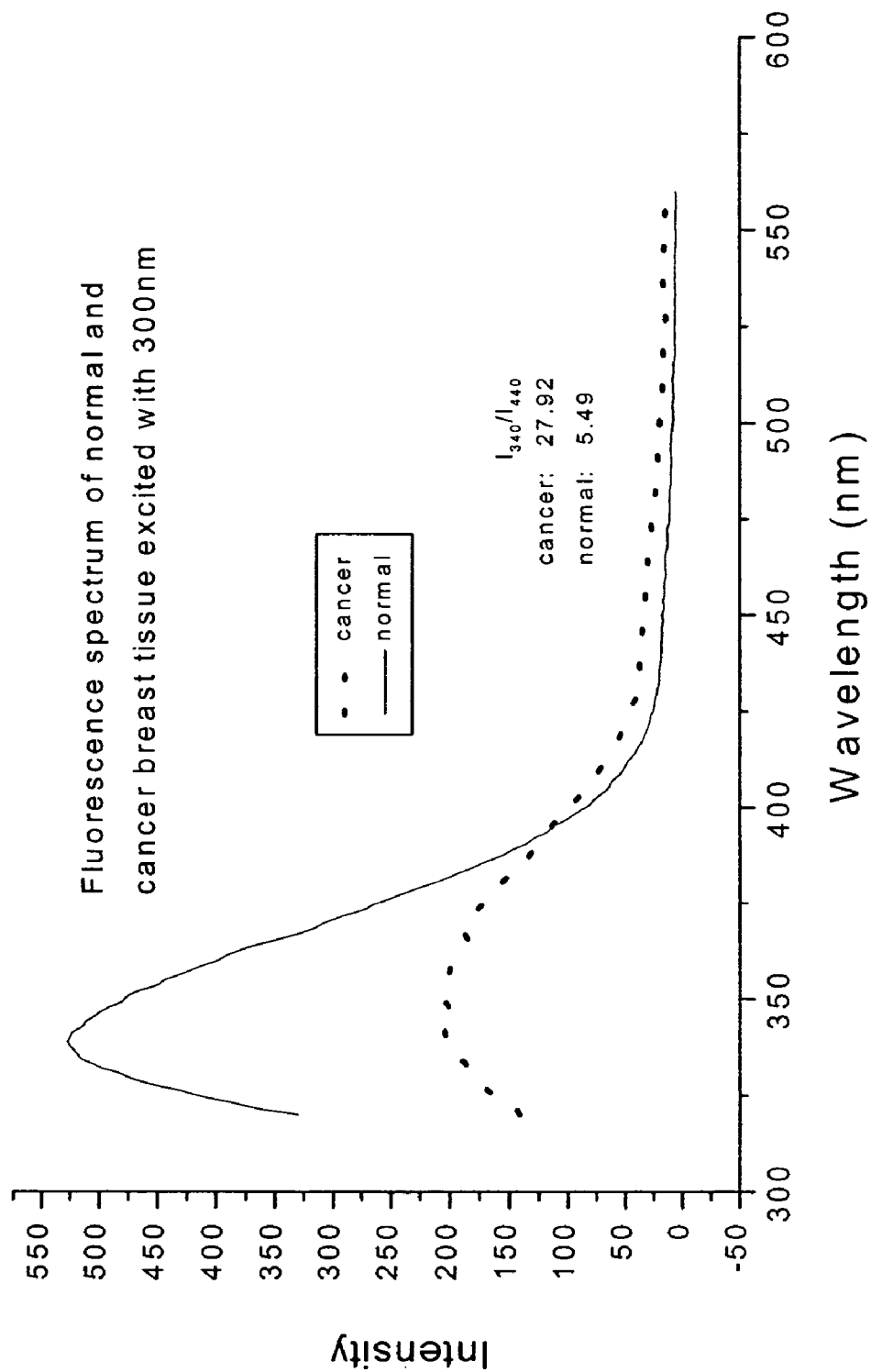
FIG. 12 shows the fluorescence spectra of normal and cancer breast tissue excited by 300 nm (same tissue as used in FIG. 8).

FIG. 12 shows the fluorescence spectra of normal and cancer breast tissue excited with 300 nm. The ratio value of $I_{340nm}/I_{440nm}$ is 27.92 and 5.49 for cancer and normal tissue. The SS and the fluorescence methods are consistent. From FIG. 12 the profile structure of fluorescence is less. The fluorescence peak of some components such as collagen and NADH did not clearly appear. Comparing FIG. 8 and FIG.

10 with FIG. 12, the SS spectrum has more structure of components even performed for one scan at fix Δλ value of 50 nm.

In conventional fluorescence spectrum, the excited wavelength is fixed in a scan. If the sample includes more than one molecular component, the fluorescence spectrum cannot locate all the peaks in one scan as illustrated in FIG. 5, and FIG. 12. One needs different excitation wavelengths to excite the different fluorescence peaks of tissue. Unlike fluorescence spectrum excited at a fixed wavelength, the excitation and emission wavelengths of the Stokes shift spectrum are scan synchronized with a fixed value of Δλ or (αv) between excitation and emission wavelength (frequency). In this way, after one scan one can obtain most of the fluorescence peaks from the different molecules present in the tissue (see FIG. 8). Since the excited and emission wavelength changes during the scan (see FIG. 7), when the Δλ value is equal to Stokes shift of a particular molecule, the excited and emission wavelength is located at the peak of the absorption and emission of the particular molecule present. The maximum of Stokes shift amplitude is reached for each different photoactive bio-molecule in tissues and cells.

The invention is not limited by the embodiments described above which are presented as examples only but can be modified in various ways within the scope of protection defined by the appended patent claims.

REFERENCES

1. B. B. Das, Feng Liu, and R. R. Alfano. "Time-resolved fluorescence and photon migration studies in biomedical and model random media." Rep. Prog. Phys. (1997) 60, 227–292. Printed in the UK.
2. Alfano R. R., D. B. Tata, J. Cordero, P. Tomashefsky, E. W. Longo and M. A. Alfano, "Laser induced fluorescence spectroscopy from native cancerous and normal tissues" IEEE J. Quantum Electron, (1984) QE-20, 1507–11.
3. Alfano R. R., Das Bidyut B., Joseph Cleary, Romulo Prudente, Edward J. Celmer. "Light sheds light on cancer-distinguishing malignant tumor from benign tissue and tumors" The Bulletin of the New York Academy of Medicine (1991). 67.143–150.
4. Alfano R. R., G. C. Tang, A. Pradhan, W. Lam, "Fluorescence spectra from cancerous and normal human breast and lung tissues." IEEE J. Quantum Electron, (1987) QE-23. 1806–11.
5. Yuanlong Yang, Edward J. Celmer, Margret Zurawska-Szczepaniak, R. R. Alfano. "Fundamental differences between malignant and benign breast tissues using an optical biopsy." Photochemistry and Photobiology. 1997, 66,(4): 518–522.
6. B. K. Ridley: "Quantum processes in semiconductors" p 237, Clarendon Press Oxford (1982).
7. B. Henderson and G. F. Imbusch. "Optical spectroscopy of Inorganic Solids" p. 197, Clarendon Press Oxford (1989).
8. R. R. Alfano and S. L. Shapiro. "Ultrafast phenomena in liquids and solids." Scientific American (1973) 228, 42–55.
9. Robert R. Alfano and Michele A. Alfano. "Method for detecting cancerous tissue using visible native luminescence" U.S. Pat. No. 4,930,516, (1990 June).
10. Robert R. Alfano. "Method and apparatus for detecting cancerous tissue using luminescence excitation spectra" U.S. Pat. No. 5,042,494, (1991 August).

We claim:
1. A method of testing a sample comprising:
   a. exciting the sample with excitation radiation and thereby generating emission radiation;
   b. varying the excitation radiation by regulating a parameter selected from the group consisting of wavelength and frequency of the excitation radiation; and
   c. synchronously scanning the excitation radiation and the emission radiation to produce a spectrum,
   wherein a constant interval between the regulated parameter of the excitation radiation and that of the emission radiation is maintained during the synchronous scanning; and
   wherein the constant interval is maintained to be substantially the Stokes shift of at least one component of the sample.
2. The method of claim 1 further comprising a step of comparing the spectrum of the sample to another sample whose condition is known.
3. The method of claim 1 wherein the sample is selected from the group consisting of tissue and cell.
4. The method of claim 3 wherein the tissue is selected from the group consisting of breast, urinary, colon, stomach, brain, prostate kidney, liver, and GYN tissue.
5. The method of claim 3 wherein the tissue comprises at least one of tryptophan, NADH, flavin and collagen.
6. The method of claim 3 wherein the sample is in a state selected from the group consisting of normal, cancer, precancer and atherosclerosis.
7. The method of claim 1 wherein the sample is tissue, and the method further comprises a step of comparing a ratio between intensities at at least two wavelengths or frequencies of the spectrum of the tissue sample to that of another tissue whose condition is known, thereby determining whether the tissue sample is cancerous, precancerous, or normal.
8. The method of claim 7 wherein the ratio between the intensities at at least two wavelengths or frequencies is the ratio between the intensities at wavelengths of about 290 nm and about 340 nm.
9. The method of claim 8 wherein the ratio between the intensities at wavelengths of about 290 nm and about 340 nm is higher for a cancerous tissue sample than the ratio for a normal tissue sample.
10. The method of claim 1 wherein the sample is tissue, and the method further comprises a step of comparing a peak position at at least one wavelength or frequency of the spectrum of the tissue sample to that of another tissue whose condition is known, thereby determining whether the tissue sample is cancerous, precancerous, or normal.
11. The method of claim 10 wherein the at least one wavelength is about 290 nm.
12. The method of claim 1 wherein the regulated parameter is wavelength, and the constant interval is about 40 to 145 nm.
13. The method of claim 12 wherein the constant interval is about 40 to 120 nm.
14. The method of claim 12 wherein the constant interval is about 50 nm.
15. The method of claim 1 wherein the regulated parameter is frequency, and the constant interval is about 5 to 500 THz.
16. The method of claim 15 wherein the constant interval is about 10 to 500 THz.
17. The method of claim 1 wherein the regulated parameter is frequency, and the constant interval is about 150 $cm^{-1}$ to 15,000 $cm^{-1}$.

18. The method of claim 14 wherein the constant interval is about 300 cm$^{-1}$ to 15,000 cm$^{-1}$.

19. The method of claim 1 wherein the sample is selected from the group consisting of bacteria, virus and other biological complex.

20. The method of claim 1 wherein the wavelength of the excitation is varied in the range of 200 to 800 nm.

21. The method of claim 1 wherein spectral pass band filters are used to filter the excitation radiation in the synchronous scanning step.

22. The method of claim 1 wherein a video system selected from the group consisting of photo-detector, CCD, CMOS, and avalanche diode is used to record the excitation radiation and the emission radiation in the synchronous scanning step.

23. The method of claim 22 wherein the video system is CCD.

24. The method of claim 1 wherein a plurality of LEDs is used to produce the excitation radiation.

25. The method of claim 1 wherein at least a portion of the excitation radiation propagates through at least one optical fiber before exciting the sample.

26. The method of claim 25 wherein the optical fiber is a component of an endoscope.

27. The method of claim 1 wherein at least a portion of the emission radiation propagates through at least one optical fiber before the emission radiation is scanned.

28. The method of claim 27 wherein the optical fiber is a component of an endoscope.

29. A method of testing a sample comprising:
   a. exciting the sample with excitation radiation and thereby generating emission radiation;
   b. varying the excitation radiation by regulating a parameter selected from the group consisting of wavelength and frequency;
   c. synchronously scanning the excitation radiation and the emission radiation to produce a first spectrum, wherein a constant interval between the regulated parameter of the excitation radiation and that of the emission radiation is maintained during the synchronous scanning;
   d. adjusting the constant interval and repeating the steps of a)–c) at least one time to produce at least a second spectrum; and
   wherein the constant interval is maintained or adjusted to be substantially the Stokes shift of at least one component of the sample.

30. The method of claim 29 further comprising a step of comparing the spectra of the sample to those of another sample whose condition is known.

31. The method of claim 29 wherein the sample is selected from the group consisting of tissue and cell.

32. The method of claim 31 wherein the tissue is selected from the group consisting of breast, urinary, colon, stomach and GYN tissue.

33. The method of claim 31 wherein the tissue comprises at least one of tryptophan, NADH, flavin and collagen.

34. The method of claim 31 wherein the sample tissue is in a state selected from the group consisting of normal, cancer, precancer, and atherosclerosis.

35. The method of claim 29 wherein the regulated parameter is wavelength, the wavelength of the excitation radiation is varied in the range of 200 to 800 nm.

36. The method of claim 29 wherein the regulated parameter is wavelength, and the constant interval is maintained or adjusted within the range of 10–145 nm.

37. The method of claim 29 wherein the regulated parameter is wavelength, and the change of the constant interval in the adjusting step of d) is in an increment within the range of 5–50 nm.

38. The method of claim 29 wherein the regulated parameter is frequency, and the constant interval is maintained or adjusted within the range of $\Delta v=5$ to 500 THz.

39. The method of claim 29 wherein the regulated parameter is frequency, and the change of the constant interval in the adjusting step of d) is in an increment within the range of 5–100 THz.

40. The method of claim 29 wherein the regulated parameter is frequency, and the constant interval is maintained or adjusted within the range of $\Delta v=150$ cm$^{-1}$ to 15,000 cm$^{-1}$.

41. The method of claim 29 wherein the regulated parameter is frequency, and the change of the constant interval in the adjusting step of d) is in an increment within the range of 50 to 3000 cm$^{-1}$.

42. The method of claim 29 wherein spectral pass band filters are used to filter the excitation radiation in the synchronous scanning step.

43. The method of claim 29 wherein a video system selected from the group consisting of CCD, CMOS, PMT, and photodetector is used to record the excitation radiation and the emission radiation in the synchronous scanning step.

44. The method of claim 29 wherein a plurality of LEDs is used to produce the excitation radiation.

45. The method of claim 29 wherein at least a portion of the excitation radiation propagates through at least one optical fiber before exciting the sample.

46. The method of claim 45 wherein the optical fiber is a component of an endoscope.

47. The method of claim 29 wherein at least a portion of the emission radiation propagates through at least one optical fiber before the emission radiation is scanned.

48. The method of claim 47 wherein the optical fiber is a component of an endoscope.

* * * * *